United States Patent

Beh et al.

[11] Patent Number: 5,851,925
[45] Date of Patent: Dec. 22, 1998

[54] STAINING TECHNIQUE FOR SEMICONDUCTOR DEVICE FOR SEM EXPOSURE

[76] Inventors: Michelle Beh, Blk 472 Jurong West St. #08-405, Singapore, Singapore, 640472; Donald Grant, #03-03 Balmeg Court, Block 6C, Balmeg Hill, Singapore, 119909

[21] Appl. No.: 678,390

[22] Filed: Jul. 2, 1996

[30] Foreign Application Priority Data

Feb. 15, 1996 [SG] Singapore ............................ 9601719-9

[51] Int. Cl.$^6$ .................................................. H01L 21/00
[52] U.S. Cl. .............................. 438/708; 438/712; 438/7; 438/8; 438/9
[58] Field of Search .................................... 438/708, 712, 438/7, 8, 9

[56] References Cited

U.S. PATENT DOCUMENTS 5,348,627  9/1994  Propst et al. .......................... 204/129.3
5,445,710  8/1995  Hori et al. ............................ 156/643.1

*Primary Examiner*—Mark Chapman
*Attorney, Agent, or Firm*—Proskauer Rose LLP

[57] ABSTRACT

A method for staining a wafer containing a semiconductor device is disclosed which properly delineates the various layers of the semiconductor device and provides good contrast for proper testing and diagnosis of problems using a scanning electron microscope. After grinding, lapping and polishing a surface of the semiconductor device, the surface is ion beam etched, reactive ion etched and stained. The staining solution is made from 1 part by volume hydrofluoric acid, 3 parts by volume nitric acid, and 6 parts by volume acetic acid. The staining solution is cooled and subjected to a light to slow the reaction of the staining solution with the semiconductor device. This prevents structure collapse and under or over etching, and provides an easily controllable staining process.

21 Claims, 3 Drawing Sheets

STAINING TECHNIQUE FOR SEMICONDUCTOR DEVICE FOR SEM EXPOSURE

FIELD OF THE INVENTION

The present invention relates to a process for staining wafers containing semiconductor devices to provide contrast of the various layers of the semiconductor devices when viewed by an SEM (Scanning Electron Microscope).

BACKGROUND OF THE INVENTION

Semiconductor devices are formed by depositing and patterning several layers of material. FIG. 1 schematically illustrates a conventional MOSFET device 10, and in particular an NMOS device. The NMOS device 10 comprises an N-type silicon substrate 11 and a P-well 12 which is formed in the substrate 11. N+ source and drain regions 14, 16, are formed at the surface of the P-well 12. The source and drain regions 14, 16, are separated by a channel 18. A gate structure is formed over the channel 18 between the source and drain regions 14, 16. More specifically, the gate 20 is formed from a conducting material such as polysilicon or polycide.

The gate 20 is separated from the surface of the P-well by a gate oxide $SiO_2$ 22. The gate 20 is covered by a dielectric 21 which may be oxide ($SiO_2$) or nitride ($Si_3N_4$). The dielectric 21 located on either side of the gate 20 forms oxide or nitride spacers 24, 26. Lightly doped regions 34 and 36 are provided to reduce the device hot carrier effects. Field oxide regions 38 are provided to separate adjacent MOS devices in an integrated circuit.

Interconnects 54, 56 directly contact the source and drain 14, 16. The interconnects 54, 56 may be metal, polysilicon or polycide. The interconnects 54, 56 may be formed in part directly over the FOX regions 38 and the dielectric 21 enclosing the gate 20. Alternatively, no interconnects 54, 56 are formed.

A Metal-Poly-Dielectric (MPD) layer 42 is deposited over the surface of the device 10. Openings are formed in the MPD layer 42 so that metal contacts 44, 46 can be made to the interconnects 54, 56. In the case where no interconnects 54, 56 are formed, the metal contacts 44, 46 directly contact the source and drain regions 14, 16.

Testing to diagnose a problem is performed on a representative wafer sample after making a group of wafers containing semiconductor devices on a silicon substrate, such as the NMOS 10 of FIG. 1, or other devices such as memory cells, bipolar junction transistors, etc. Conventional testing involves a method of removing and staining the various layers that form the device under test. Staining delineates the various layers and provides better contrast for viewing the device using an SEM (Scanning Electron Microscope).

FIG. 2 shows a flow chart of a conventional method 200 for staining wafers containing semiconductor devices used to delineate the various layers and improve contrast. The stained semiconductor devices of the wafer are viewed by an SEM. However, despite improved contrast as compared to unstained semiconductor devices, the semiconductor devices stained using the conventional method 200 suffer from poor contrast among the various materials. As shown in FIG. 2, the surface of the wafer containing semiconductor devices is prepared for staining as a follows:

1. a. In step 205, grinding the surface of the wafer is performed by first using diamond films with progressively smaller sizes.
   b. In step 210, lapping the ground wafer surface is performed using diamond films.
   c. In step 215, polishing the sample with colloidal silica is performed using nap cloth.
2. In step 220, staining of P-N junctions is performed for 8 seconds using a conventional staining solution comprising:
   1 part by volume Hydrofluoric acid;
   3 parts by volume Nitric acid; and
   6 parts by volume Acetic acid.
3. In step 225, covering the wafer with a conductive metal coating is performed to dissipate charges induced during SEM operation.
4. In step 230, subjecting the wafer to a 10 kv to 30 kv scanning electron beam of an SEM is performed for observation and diagnosis of any problems.

The staining solution stains the dielectric materials but leaves the metals lightly stained. Junction staining is performed to provide contrast in the junctions between the dielectric materials and the metals, such as the metal contacts 44, 46 or the metal interconnects 54, 56. A better contrast allows for better observation of the structure under an SEM.

Such a conventional junction staining suffers from a controllability problem since the staining time is critical. If the staining duration using the staining solution is too long, then the junctions are over etched. This may cause structure collapse, such as collapse of the source and drain 14, 16 (FIG. 1). If the staining duration is too short, then the dielectric materials are not stained properly and the metal structures are not delineated. Thus, contrast is poor.

The metal coating used after staining the wafer with the staining solution is often thick. This results in loss of surface information due to being covered by the metal coating layer.

In view of the foregoing, it is an object of the present invention to provide a method for staining a semiconductor device which overcomes the shortcomings of the prior art.

Specifically, it is an object of the present invention to provide a method for staining a semiconductor device which better delineates the various materials and layers of the semiconductor device and improves contrast.

It is another object of the present invention to provide a method for staining a semiconductor device which is easily controllable, and prevents under or over etching and structure collapse.

It is yet another object of the present invention to provide a method for staining a semiconductor device which eliminates the need for metal coating thus preventing loss of surface information, and allowing for an unhindered view of the semiconductor device.

SUMMARY OF THE INVENTION

A method for staining a wafer containing a semiconductor device in accordance with an illustrative embodiment of the invention comprises the following steps:

(1) ion beam etching a polished surface of the semiconductor device, e.g., for approximately 5 minutes, using approximately 9 kv of beam voltage level, under a 90° tilt;

(2) reactive ion etching the ion beam etched surface of the semiconductor device, using, e.g., 40 parts by volume $CF_4$, and 10 parts by volume of $O_2$, and performed for approximately 4 sec, with a power of approximately 150 w and a pressure of approximately 150 mTorr;

(3) staining the semiconductor device by cooling a staining solution to approximately 5° C.; and (4) illuminating the cooled staining solution.

During the illuminating step, the semiconductor device is immersed in the cooled staining solution. The ion beam and reactive ion etching steps enhance a view of metal contacts of the semiconductor device, while the staining step delineates dielectric layers of the semiconductor device.

Illustratively, the staining solution is made from 1 part by volume hydrofluoric acid, 3 parts by volume nitric acid, and 6 parts by volume acetic acid. A halogen lamp, for example, is used to illuminate the cooled staining solution. Illuminating the cooled staining solution slows the reaction of the staining solution. This prevents structure collapse and under or over etching, and provides an easily controllable staining process.

Prior to ion beam etching, the surface of the semiconductor device is prepared by grinding, lapping and polishing. Illustratively, grinding is performed using diamond films having progressively smaller sizes, e.g., having sizes of 30 $\mu$m, 15 $\mu$m, and 6 $\mu$m. Diamond films, e.g., having sizes of 3 $\mu$m and 1 $\mu$m, are used for lapping. Polishing may be performed with colloidal silica having a size of 0.05 $\mu$m using nap cloth.

The stained wafer containing semiconductor devices is provided with a conductive path using carbon tape, copper tape, or silver paste. Illustratively, the conductive path is located on the surface of the wafer and is connected to ground. The conductive path dissipates electrical charges induced by the electron beam of the scanning electron microscope, for example. Next, the semiconductor device is scanned with an electron beam of a scanning electron microscope. Illustratively, scanning is performed using a voltage from approximately 2.5 Kev to approximately 5 Kev.

The present invention results in a stained semiconductor device that does not have a metal coating, is better delineated, and has improved contrast. The inventive method is easily controllable, and prevents under or over etching and structure collapse. This allows for proper testing and diagnosis of problems using an SEM.

DETAILED DESCRIPTION OF THE INVENTION

The present invention is directed to a method for staining a wafer containing a semiconductor device which prevents structure collapse and over or under etching, eliminates metal coating, and provides better contrast for viewing under an SEM.

Figure 3:
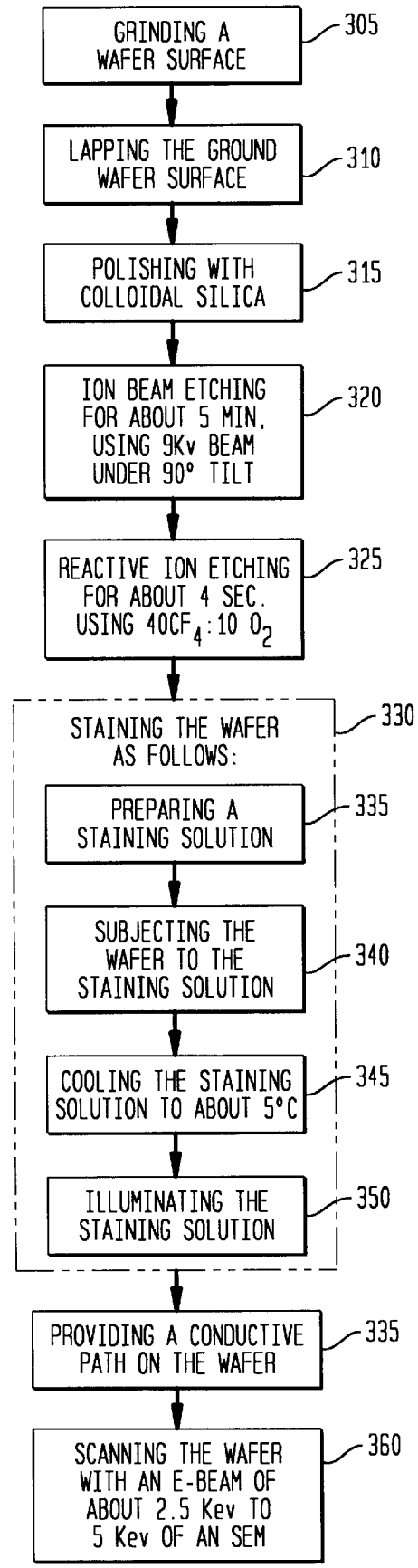
FIG. 3 illustrates a flow chart of a method for staining wafers containing semiconductor devices according to the present invention.

FIG. 3 shows a flow chart of a method 300 for staining wafers containing semiconductor devices according to the present invention. As shown in FIG. 3, the inventive method involves the following steps to stain the surface of the wafer:

1. As in the conventional method, grinding, lapping and polishing of the surface of the wafer are performed. A detailed description of these steps include:
   a. In step 305, grinding the surface of the wafer by first using diamond films with progressively smaller sizes. For example, a diamond film having a size of 30 $\mu$m is first used. Next, 15 $\mu$m and 6 $\mu$m diamond films are used;
   b. In step 310, lapping the ground wafer surface of the wafer using diamond films having a size of 3 $\mu$m and 1 $\mu$m, respectively; and
   c. In step 315, polishing the surface of the wafer with colloidal silica having a size of 0.05 $\mu$m using nap cloth.

2. In step 320, subjecting the polished surface of the wafer to ion beam etching for approximately 5 minutes is performed, using approximately 9 kv of beam voltage level, under 90° tilt. That is, the angle of incidence of the ion beam on the specimen is 90°.

The ion beam etching step 320 micro-finishes the sample surface to delineate the hard structure material like tungsten from its surrounding soft metal, such as the MPD layer 42 and the interconnects 54, 56.

3. In step 325, reactive ion etching is performed using, for example, 40 part by volume $CF_4$ and 10 parts by volume of $O_2$. Illustratively, the reactive ion etching is performed for approximately 4 sec, with a power of approximately 150 w and a pressure of approximately 150 mTorr.

Figure 1:
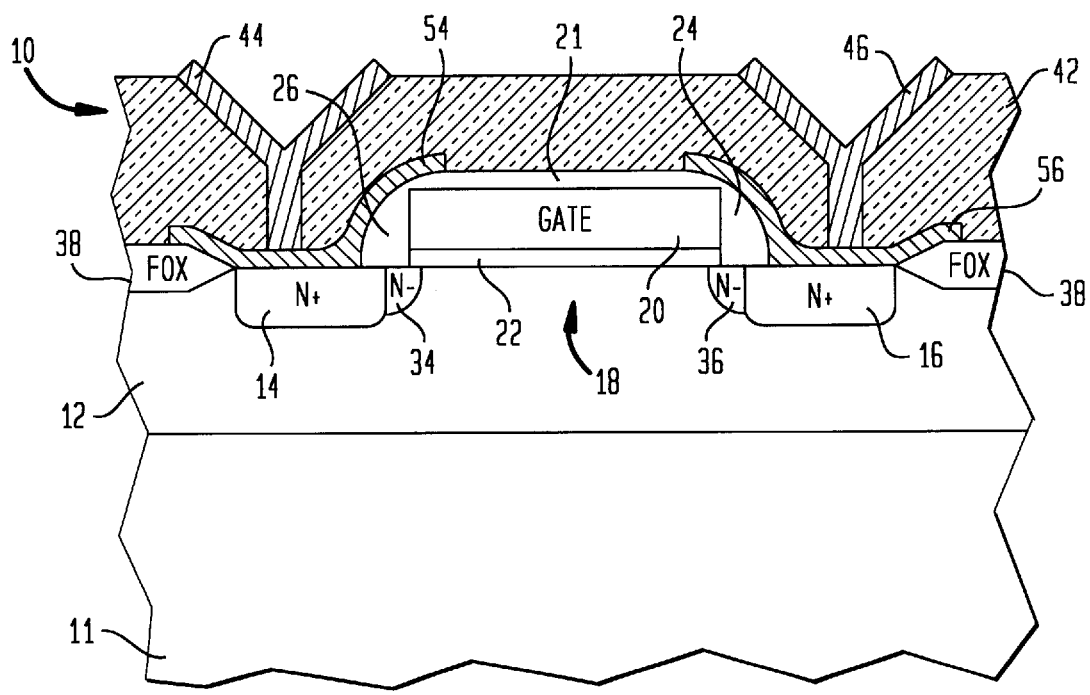
FIG. 1 illustrates a conventional MOS device.

The ion beam etching step 320 and reactive ion etching step 325 are not performed in conventional staining methods. The reactive ion etching step 325 etches and delineates the different dielectric layers, e.g., BPSG (borophosphosilicate glass), oxide ($SiO_2$), nitride ($Si_3N_4$), or other dielectric layers formed by various processes, such as by PECVD (Pressure Enhanced Chemical Vapor Deposition). These two etching steps, the ion beam step 320 and reactive ion etching step 325, enhance the view of the metal contacts 44, 46 (FIG. 1).

4. In step 330, staining the junctions between the different dielectrics and between the metal contacts 44, 46 (FIG. 1) and the underlayers, to delineate the various dielectric materials, such as the oxides, is performed as follows:
   a. In step 335, preparing the conventional staining solution made of 1 part by volume hydrofluoric acid, 3 parts by volume nitric acid, and 6 parts by volume acetic acid.
   b. In step 340, subjecting the wafer to the staining solution.
   c. In step 345, cooling the staining solution to approximately 5° C.
   d. In step 350, shining a strong halogen light.

When the semiconductor device is illuminated in step 350, the semiconductor device is immersed in the cooled staining solution. Nitric and acetic acids are sensitive to light. Therefore, the reaction of the nitric and acetic acids with the wafer can be slowed and controlled by cooling the staining solution and shining a light thereon. This greatly enhances controllability of the junction staining, and prevents over or under etching, thus preventing structure collapse.

5. In step 355, providing a conductive path to the wafer under test is performed by using, for example, carbon tape, copper tape, or silver paste. The conductive path is provided on the surface of the wafer and is connected to ground. The conductive path dissipates electrical charges induced during SEM operation, e.g., induced by the electron beam of the scanning electron microscope.

6. In step 360, subjecting the wafer to a scanning electron beam of an SEM is performed for observation and diagnosis of any problems. Illustratively, the voltage level of the scanning electron beam is from approximately 2.5 Kev to approximately 5 Kev.

Figure 2:
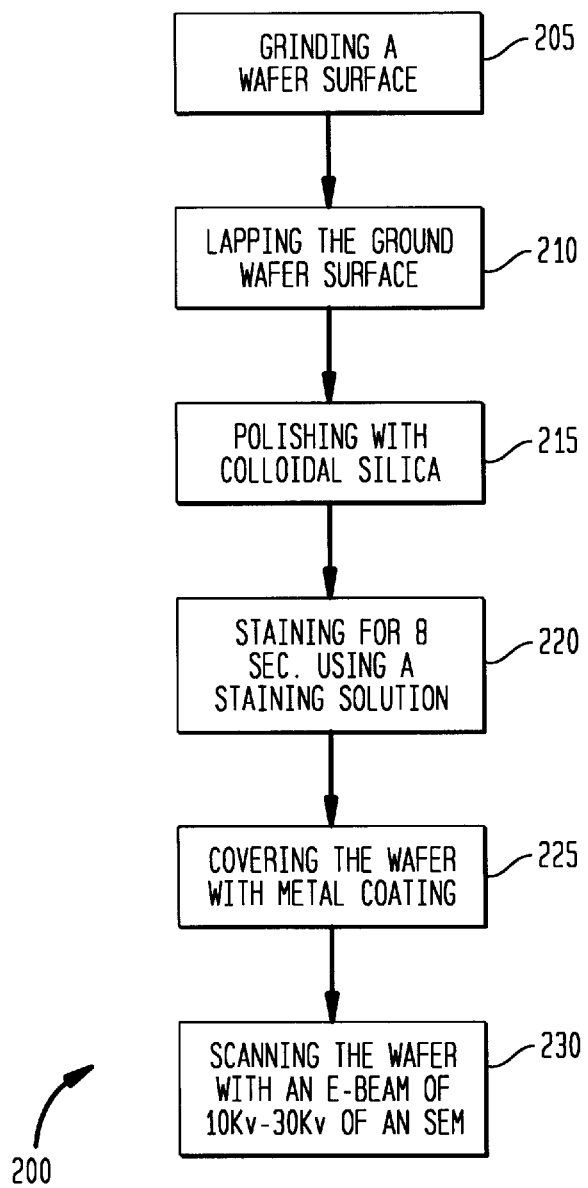
FIG. 2 illustrates a flow chart of a conventional method for staining wafers containing semiconductor devices.

Unlike a wafer stained using the conventional method 200 shown in FIG. 2, a wafer surface stained using the inventive method 300 of FIG. 3 has good contrast among the various types of material.

The advantages of the inventive method include:

1. The ion beam etch, performed in step 320, and the RIE etch, performed in step 325, sufficiently delineate the metal parts from the rest of the structure.
2. Etching the junction is easily controlled since the staining solution is cooled down to slow down the etching.
3. The metal, which does not require much etching and delineation, is etched slightly by the cooled nitric acid. Cooling of the nitric acid reduces its etching characteristic thereby etching the metal only slightly.

Finally, the above described embodiments of the invention are intended to be illustrative only. Numerous alternative embodiments and equivalent methods may be devised by those skilled in the art without departing from the scope of the following claims.

The claimed invention is:

1. A method for staining a wafer containing a semiconductor device comprising the steps of:
   (1) ion beam etching a polished surface of the semiconductor device;
   (2) reactive ion etching the ion beam etched surface of the semiconductor device;
   (3) staining the semiconductor device by cooling a staining solution; and
   (4) illuminating the cooled staining solution to control a reaction of said staining solution with said semiconductor device.

2. The method of claim 1, wherein the ion beam etching is performed for approximately 5 minutes, using approximately 9 kv of beam energy, under a 90° tilt.

3. The method of claim 1 further comprising, before the step of ion beam etching, the steps of:
   (a) grinding the semiconductor device;
   (b) lapping the ground semiconductor device; and
   (c) polishing the lapped semiconductor device.

4. The method of claim 3, wherein said grinding step is performed by using diamond films having progressively smaller sizes.

5. The method of claim 3, wherein said grinding step is performed by first using a diamond film having a size of 30 $\mu$m, second by using a diamond film having a size of 15 $\mu$m, and third by using a diamond film having a size of 6 $\mu$m.

6. The method of claim 3, wherein said lapping step is performed by using diamond films having progressively smaller sizes.

7. The method of claim 3, wherein said lapping step is performed by first using a diamond film having a size of 3 $\mu$m, and next by using a diamond film having a size of 1 $\mu$m.

8. The method of claim 3, wherein said polishing step is performed using colloidal silica having a size of 0.05 $\mu$m using nap cloth.

9. The method of claim 1, wherein said reactive ion etching step is performed using a mixture of $CF_4$ and $O_2$.

10. The method of claim 1, wherein said reactive ion etching step is performed using 40 parts by volume $CF_4$, and 10 parts by volume of $O_2$.

11. The method of claim 9, wherein said reactive ion etching step is performed for approximately 4 sec, with a power of approximately 150 w and a pressure of approximately 150 mTorr.

12. The method of claim 1, wherein said ion beam and reactive ion etching steps enhance a view of metal contacts of the semiconductor device.

13. The method of claim 1, wherein said staining step delineates dielectric layers of the semiconductor device.

14. The method of claim 1, wherein said staining step comprises cooling said staining solution to approximately 5° C.

15. The method of claim 1, wherein the staining step cools the staining solution made of 1 part by volume hydrofluoric acid, 3 parts by volume nitric acid, and 6 parts by volume acetic acid.

16. The method of claim 1, wherein said step of illuminating said staining solution staining solution is carried out with a halogen lamp.

17. The method of claim 1 further comprising the step of providing a conductive path to the semiconductor device for dissipating electrical charges caused by an electron beam of a scanning electron microscope.

18. The method of claim 1 further comprising the step of scanning the semiconductor device with an electron beam of a scanning electron microscope.

19. The method of claim 18, wherein the scanning step is performed using a voltage level of approximately 2.5 Kev to approximately 5 Kev.

20. A method for diagnosis of defects in a wafer containing a semiconductor device comprising the steps of:
   (1) ion beam etching a polished surface of the semiconductor device;
   (2) reactive ion etching the ion beam etched surface of the semiconductor device;
   (3) staining the semiconductor device by placing said semiconductor device in contact with a staining solution and slowing a reaction rate of said staining solution with said semiconductor device using an external stimulus;
   (4) providing a conductive path to the semiconductor device using one of carbon tape, copper tape, and silver paste; and
   (5) scanning the semiconductor device with an electron beam of a scanning electron microscope.

21. The method of claim 20, wherein said external stimulus is light from a halogen lamp.

* * * * *

UNITED STATES PATENT AND TRADEMARK OFFICE
CERTIFICATE OF CORRECTION

PATENT NO : 5,851,925
DATED : December 22, 1998
INVENTOR(S) : Michele BEH; Donald GRANT It is certified that error appears in the above-identified patent and that said Letters Patent is hereby corrected as shown below:

On the title page: Item [73]

The Assignee should read:
Institute of Microelectronics, Singapore, Singapore

Signed and Sealed this

Ninth Day of November, 1999

Attest:

Attesting Officer

Q. TODD DICKINSON

Acting Commissioner of Patents and Trademarks